(12) United States Patent
Scaife

(10) Patent No.: US 11,219,557 B2
(45) Date of Patent: Jan. 11, 2022

(54) CUSTOMIZED FAST MOVING CONSUMER GOODS PRODUCTION SYSTEM

(71) Applicant: Martin Scaife, Singapore (SG)

(72) Inventor: Martin Scaife, Singapore (SG)

( * ) Notice: Subject to any disclaimer, the term of this patent is extended or adjusted under 35 U.S.C. 154(b) by 318 days.

(21) Appl. No.: 15/745,844

(22) PCT Filed: Aug. 19, 2016

(86) PCT No.: PCT/SG2016/050405
§ 371 (c)(1),
(2) Date: Jan. 18, 2018

(87) PCT Pub. No.: WO2017/014696
PCT Pub. Date: Jan. 26, 2017

(65) Prior Publication Data
US 2018/0208346 A1   Jul. 26, 2018

(30) Foreign Application Priority Data
Jul. 21, 2015   (GB) .................................... 1512819

(51) Int. Cl.
*B65B 59/02*   (2006.01)
*B65B 35/04*   (2006.01)
(Continued)

(52) U.S. Cl.
CPC ........ *A61F 13/15804* (2013.01); *A41D 13/11* (2013.01); *A41D 27/08* (2013.01);
(Continued)

(58) Field of Classification Search
CPC .. B65B 57/20; B65B 5/06; B65B 5/08; B65B 5/10; B65B 5/12; B65B 25/14;
(Continued)

(56) References Cited

U.S. PATENT DOCUMENTS 4,560,057 A   12/1985   Applegate et al.
5,074,096 A * 12/1991   Focke ..................... B65B 35/04
53/133.5
(Continued)

FOREIGN PATENT DOCUMENTS

CN   2860444 Y * 1/2007   ............. A61F 13/15
CN   2860444 Y * 1/2007   ............. A61F 13/15
(Continued)

*Primary Examiner* — Hemant Desai
*Assistant Examiner* — Jacob A Smith
(74) *Attorney, Agent, or Firm* — Jacob M. Ward; Ward Law Office LLC

(57) ABSTRACT

A manufacturing method for customized fast moving consumer goods (FMCG) comprising the production of the customized goods in a main production process stream or a side stream. The method further comprises temporarily storing the customized goods in a side stream process and subsequently re-inserting said goods into the main production process stream. The customized goods may be finally packaged in a dedicated pack or in a pack that also contains non-customized goods. The method is suitable for, but not limited to, articles such as diapers, absorbent products, tissues and other hygienic products.

14 Claims, 13 Drawing Sheets

(51) Int. Cl.

| | |
|---|---|
| *B65B 57/20* | (2006.01) |
| *A61F 13/15* | (2006.01) |
| *B65B 5/00* | (2006.01) |
| *B65G 47/51* | (2006.01) |
| *A41D 13/11* | (2006.01) |
| *A41D 27/08* | (2006.01) |
| *A61F 13/551* | (2006.01) |
| *G06Q 30/06* | (2012.01) |
| *G06Q 50/04* | (2012.01) |
| *G06Q 50/28* | (2012.01) |
| *A61F 13/84* | (2006.01) |

(52) U.S. Cl.
CPC ............ *A61F 13/5519* (2013.01); *B65B 5/00* (2013.01); *B65B 35/04* (2013.01); *B65B 57/20* (2013.01); *B65G 47/5113* (2013.01); *G06Q 30/0621* (2013.01); *G06Q 50/04* (2013.01); *G06Q 50/28* (2013.01); *A61F 2013/8476* (2013.01); *A61F 2013/8497* (2013.01); *B65B 2210/04* (2013.01); *B65B 2220/14* (2013.01); *Y02P 90/30* (2015.11)

(58) Field of Classification Search
CPC ..... B65B 25/141; B65B 25/145; B65B 35/30; B65B 35/35; B65B 35/405; B65B 35/44; B65B 35/54; B65B 59/00; B65B 63/04; B65B 65/00; B65B 65/003
USPC ......... 53/443, 445, 474, 147, 154, 155, 235, 53/237, 238, 152, 153, 502, 501
See application file for complete search history.

(56) References Cited

U.S. PATENT DOCUMENTS

| | | | | |
|---|---|---|---|---|
| 5,373,680 A * | 12/1994 | Munsch | ................... | B65B 63/04 198/369.1 |
| 5,551,209 A * | 9/1996 | Molina | ................... | B65B 35/04 198/444 |
| 5,706,632 A * | 1/1998 | Kivits | ................... | B65H 29/60 271/3.19 |
| 6,092,532 A * | 7/2000 | Focke | ................... | B65B 19/02 131/280 |
| 8,627,639 B2 * | 1/2014 | Ali | ................... | B65B 5/103 53/473 |
| 8,650,844 B2 * | 2/2014 | Romanyszyn | ............ | B65B 1/04 53/512 |
| 8,892,240 B1 * | 11/2014 | Vliet | ................... | B65G 1/1378 700/216 |
| 8,943,785 B2 * | 2/2015 | Blickhan | ................ | A01F 12/50 53/500 |
| 2002/0152001 A1 * | 10/2002 | Knipp | ................... | G06Q 10/087 700/100 |
| 2005/0097866 A1 * | 5/2005 | Hudetz | ................... | B41J 13/103 53/474 |
| 2008/0097857 A1 | 4/2008 | Walker et al. | | |
| 2010/0300309 A1 | 12/2010 | Schneider | | |
| 2011/0011490 A1 * | 1/2011 | Rodrigues | ........... | B01F 13/1055 141/11 |
| 2012/0186192 A1 * | 7/2012 | Toebes | ................. | B65G 17/123 53/235 |
| 2013/0074453 A1 * | 3/2013 | Walsh | ................... | B65B 25/04 53/443 |
| 2013/0097975 A1 * | 4/2013 | Bailey | ................... | B65B 35/54 53/473 |
| 2013/0205723 A1 * | 8/2013 | Blake | ................... | G07D 9/00 53/473 |
| 2014/0157731 A1 * | 6/2014 | Perazzo | ................... | B65B 5/045 53/473 |
| 2014/0223860 A1 * | 8/2014 | Schmid | ................... | B65B 3/025 53/411 |
| 2014/0230374 A1 * | 8/2014 | Tian | ................... | G06Q 10/04 53/445 |
| 2014/0245701 A1 * | 9/2014 | Loevenich | ............. | B65B 63/02 53/443 |
| 2014/0260104 A1 * | 9/2014 | Ackley | ................... | B07C 5/34 53/443 |
| 2014/0303774 A1 * | 10/2014 | Schwarzli | ............ | B65B 59/001 700/233 |
| 2015/0053138 A1 * | 2/2015 | Ramsey | ................... | B65B 69/00 119/61.5 |
| 2015/0059286 A1 * | 3/2015 | Vazul | ................... | B65B 35/243 53/244 |
| 2015/0068160 A1 * | 3/2015 | Kudrus | ................... | B65H 39/06 53/447 |
| 2015/0130201 A1 * | 5/2015 | Crosby | ................ | B65G 47/918 294/188 |
| 2015/0166217 A1 * | 6/2015 | Deutschle | ............ | B65B 7/2842 53/425 |

FOREIGN PATENT DOCUMENTS

| | | |
|---|---|---|
| EP | 1021362 A1 | 7/2000 |
| WO | 2005067434 A2 | 7/2005 |
| WO | 2006002980 A1 | 1/2006 |

* cited by examiner

CUSTOMIZED FAST MOVING CONSUMER GOODS PRODUCTION SYSTEM

CROSS-REFERENCE TO RELATED APPLICATIONS

This patent application is a United States National Stage Patent Application of PCT/SG2016/050405, filed Aug. 19, 2016, which in turn claims the benefit of Great Britain Patent Application No. GB1512819.2, filed Jul. 21, 2015. The entire disclosures of the above patent applications are hereby incorporated herein by reference.

TECHNICAL FIELD

The present invention relates to a method of customizing fast moving consumer goods (FMCGs) including but not limited to products such as absorbent articles such as diapers for babies or adults, training pants, pull-up diapers (diaper pants), sanitary napkins, panty liners and also non absorbent articles such as condoms, face masks, tissues, toilet paper, wipes, health care, hair and beauty related products, etc., which are sold to end-consumers in a certain package comprising several of such articles and which are produced on continuously operating high speed manufacturing lines. The articles within such pack(s) and/or the packs themselves are customized during production so as to match a particular feature as ordered by a specific customer prior to production. These customizing features are implemented in the product during manufacturing and a predetermined number of articles are compiled in a pack. The pack may consist entirely of customized articles or partially consist of customized articles. The present invention relates to a manufacturing process allowing the pursue of pack or product-customization in a versatile manner even if the manufacturing process is interrupted and/or if a full batch of products with varying features is not successfully made, e.g. due to quality control reasons. The present invention also relates to the manufacturing equipment for such a manufacturing process.

Today these products are typically made on high-speed production systems according to a specific product design (typically described in a formula card) and a significant equipment re-configuration and/or process re-configuration is required to parts and/or systems of the manufacturing system (typically referred to as a size change) to enable the manufacturing system to produce a product according to a new formula card. After the subsequent size change has been completed, products are produced again at high speed according to the new formula card. Currently any form of FMCG customization involves many manual steps including liaison with the customizer, dedicated product design and even once the customized products have been produced, significant manual effort is still required in the packaging efforts and supply chain management to ensure the customizer's order is successfully fulfilled. Furthermore, many customization manufacturing processes (such as inkjet printing and associated ink drying time) have limited capability to run at high production surface speeds and many of the customization processes which actually have the capability to run at high speeds are typically expensive to procure and/or have high production operational costs. Embodiments according to the present invention relate to a new system to manage the overall supply chain of the customization process and the manufacturing of customized FMCG products either at full production speed or at a slower speed in parallel to the main manufacturing process with the subsequent in-feeds of the finished customized components and/or assemblies at a higher production speed of the original customization processes thereby not having any significant impact on the efficiency of the main manufacturing process.

BACKGROUND

Today, consumers of FMCGs typically purchase their products at a convenience store, supermarket or via the Internet. Such FMCGs are typically produced at high speed on dedicated manufacturing systems where thousands of products can be made each minute and where multi-million dollar investments are required to purchase such manufacturing equipment. As the depreciation cost for such assets is as a consequence very high and with operating costs for such equipment also of financial significance, such that companies operating in such a production environment typically focus their efforts on enhancing production speeds, reducing down-time caused by size change and respective process set-ups and work towards increasing overall production efficiency. In such a production environment, making individually customized products which are individually designed and specified by the consumer, has to date been met with widespread refusal. With many other significant limiting factors hindering customization such as in many cases the slower production speeds of equipment and processes which are capable to individually customize individual products (such as inkjet printing together with the respective ink drying time) and the significant amount of human-to-human contact required during today's customization process, the feasibility of any kind of broader scaled customization activities in the FMCG sector is limited.

As a result customization is carried out on an extremely small percentage of overall FMCG shipment volumes and in many categories, customized products account for less than 0.05% of overall shipment volumes with some product categories having no customization at all. Any new methods to automate the customization process of FMCG products and reduce the respective costs will open up new niches within the FMCG industry. Whilst it is not expected that FMCG customization will become "mainstream" where 100% of total product shipments would be customized in the near future, a higher percentage of overall shipment volumes compared to today would be customized in the future should the price points be viable and the overall process be automated. In some FMCG categories the expected volume of customized product could range between 0.75%-8.5% of non-customized production volumes.

Recently however, there has been an explosion in personnel computer & mobile devices, these devices not only have the capability to order FMCG products such as via e.g. Amazon™ or directly at the supermarket for home delivery but also have the processing power and capability to design customized FMCG products such as a customized artwork design and/or specifying and/or defining other product features. Producing such small volumes of any one SKU (stock keeping unit, with a SKU having a batch quantity of one or more), on such high-speed production systems has to date not been viable and typically today, if any form of product customization is carried out, this effort is usually carried out at a separate location to the main production process or even by dedicated companies who customize products typically through the modification of existing products according to their customer's requirements.

In WO2005/067434 a process is described of organising a plurality of goods or products into a plurality of distinct groups of products specifically according to a customer's request and focusing to respective storage capacity calculations of the subsequent storage and shipping medium, however, the disclosure fails to address any aspects of the customization in relation to the manufacturing process.

In US2008/00978575 a process is described where a consumer may select or specify features of an absorbent paper product and its packaging. The publication, however, does not address the production related issues of such a product, and also does not address the problems in relation to the logistical management and re-ordering of the products when a production interruption occurs.

Equally, a significant amount of prior art exists in the field related to the packaging processes of FMCG products. One of these examples is outlined in EP1021362 where an additional process is added to a stacker chain that is capable to expel defective articles from the process. There is however no prior that described the addition of a temporary storage device to such a stacker chain which can be used to addresses issues behind the logistical management of customized FMCG products during their respective production process and no prior art outlining the inventions required in the overall production process to allow the respective production of the customized product(s) in parallel to the main production process.

SUMMARY

In a first aspect, the present invention relates to a process for the manufacture of Fast Moving Consumer Good (FMCG) products, comprising the steps of
  producing a continuous series of a first plurality of products in a continuous main stream production process prior to the packing;
  producing a series of between 2 to 10 000 of at least a second plurality of products differing in predetermined customizing features from the first plurality of products in a continuous production process that may be a particular process step within the main stream production process or a side stream production process;
  storing a sub-set or all of the second plurality of products in an interim storage device in a side stream of the main stream product process for between 1 millisecond and 10 years;
  re-feeding products of the second plurality of products from the interim storage device back into the main stream production process towards the packing,
  packing a predetermined number of the second plurality of products into the same pack, optionally comprising a predetermined number of the first plurality of products.

The process may further comprise the steps of
conveying a plurality of the second plurality of FMCG products in a machine or cross machine direction to an in-feed of a moving stacker, the stacker comprising a plurality of product receiving means, preferably fingers, cassettes, or auger flights, adapted to receive at least one FMCG product;
sequentially inserting at least one product of the second plurality of FMCG products into at least one product receiving means at the in-feed of the stacker such that a plurality of the FMCG products is provided within a plurality of the product receiving means;
transporting the FMCG products in the product receiving means towards an extraction station comprising an extraction device;
removing at least one FMCG product from the product receiving means of the stacker by the extraction device into a temporary storage device, optionally repeating this step until the temporary storage device comprises a predetermined number of products of the second plurality of products;
re-feeding the predetermined number of products stored in the temporary storage device back into the main stream production process or towards a secondary stacker system.

In another aspect, a method relates to producing customized FMCG products concurrently with manufacturing standard products in a main stream production process, the method comprising the following steps:
  receiving an order from a customizer, the order comprising shipment related data, design related data, and order counts for specific customized product(s), preferably via an internet connected system;
  optionally analysing received order data and rejecting any orders that do not conform to a predetermined code of practise;
  converting the design related data into a format compatible with the production process control system;
  optionally preparing customized raw material(s) or product components or product sub-assemblies according to customizer's order in a side stream of the main stream production process, preferably operated at a process speed lower than the main stream production process speed;
  modifying the main stream production process such that customized products are produced or the customized raw material(s) or product components or product sub-assemblies are introduced to the main stream production process;
  temporarily storing customized products, optionally producing further customized products until the order count is fulfilled;
  feeding the order count of the temporarily stored customized products into the main stream production process;
  packing the order count of customized product into a dedicated customized order pack or adding the order count of customized product into a pack that comprises non-customized products.
  connecting the customized products with the shipment related data;
  dispatching the customized products to the customizer.

Any of the processes according to the present invention may comprise a "pick & place" process step for customizing products, optionally by applying an RFID tag to a product and/or a bag or box comprising customized products and/or the step of adding an add-on, such as dry or wet tissue(s) or wipe(s) to a hygienic product, such as an absorbent article, comprising a topsheet and a backsheet, whereby the add-on is optionally located between the top sheet and back sheet and which has the capability to be removed through either the top sheet or back sheet or between the top sheet or back sheet without rendering the hygiene product unusable.

In another aspect, the present invention is a Fast Moving Consumer Goods (FMCG) production process comprising the steps of producing a continuous series of products, which exhibit customizing features and packing an array of products with common customizing features into a pack.

The process further comprises the steps of
  receiving between 1 to 10 000 products from a continuous product stream prior to the packing;
  storing between 1 to 10 000 products for between 1 millisecond and 10 years year;

re-feeding between 1 to 10 000 products back into the product stream towards the packing, packing only products with common customizing features into the same relevant pack.

The products with customizing product features may be packed such that a predetermined number of packs are packed after a portion of the predetermined number is temporarily stored until the predetermined number can be packed into one pack. The equipment useful for such a manufacturing process for the high speed production of series of products comprising customizing features, the equipment may comprise a product assembly part comprising a customizing equipment for producing a stream of products;

a packing part, adapted to pack a predetermined amount of products of the stream of products into a pack;

an interim product storage device for receiving products with one or differing customizing features adapted to re-feed products with same customizing features into the stream of products;

such that a pack comprises the predetermined amount of products of the same customizing features.

The process may further be executed by using a storage device, where single or multiple products can be inserted into the device. The storage device may further have a manual or semi-automatic or fully automatic sealing device, that allows the storage device to be fully closed to prevent contamination risk during times of non-production such as machine downtime and/or maintenance. The products as may be produced by using the manufacturing process or on the manufacturing equipment may have been customized via a customizer which is connected by electronic means, either directly or indirectly to the FMCG production process. The storage device may have between 1-1000 chambers with each chamber capable of holding between 1-1000 products, and it may move in an orientation other than the orientation of the product flow to allow products to be inserted and stored in more than 1 chamber. The storage device may move in an orientation similar to the orientation of the product flow into a phased position with the product flow to allow re-ordered products to be inserted into defined locations within the storage device. The transport medium of the products may be a stacker chain, a conveyor, or an auger.

The FMCG production process may comprise a temporary product storage device, either of automatic or semi-automatic operation, located between the final product-cutting cutting process and final secondary packaging sealing process capable of receiving between 1 to 10 000 products and/or store between 1 to 10 000 products and/or re-feeding between 1 to 10 000 products back into the product between 1 millisecond and 10 years year after the products entered the device. With this storage device incomplete orders can be stored in this storage device until missing product orders are fulfilled, and/or incomplete orders can be stored in this storage device and where replacement orders are sent to the storage device and upon completion of order, where the completed order is then deposited back into the original product stream from where the products where received or into a different product stream other from where the products where received. With this storage device single or multiple products can be inserted into the device. The storage device may have a manual or semi-automatic or fully automatic sealing device that allows the storage device to be fully closed to prevent contamination risk during times of non-production such as machine downtime and/or maintenance.

For this storage device the products produced may have been customized via a customizer who is connected by electronic means, either directly or indirectly to the FMCG production process, and the storage device may comprise between 1-1000 chambers with each chamber capable of holding between 1-1000 products.

The storage device may move in an orientation other than the orientation of the product flow to allow products to be inserted and stored in more than 1 chamber.

The storage device may move in an orientation similar to the orientation of the product flow into a phased position with the product flow to allow re-ordered products to be inserted into defined locations within the storage device. The transport medium of the products may be a stacker chain, a conveyor, or an auger.

The invention further relates to a method of providing a temporary storage for FMCG products during a high speed manufacturing process, wherein the method comprises the steps of— conveying of a plurality of FMCG products in a machine or cross machine direction to an in-feed of a transport means, preferably a moving stacker, the stacker including a plurality product receiving means, such as fingers or cassettes or flights of an auger, each receiving means being configured to receive at least one FMCG product;

sequentially inserting at least one FMCG product into at least receiving means, such as one finger or cassette at the in-feed of the stacker such that a plurality of FMCG products is provided within the receiving means;

transporting the FMCG products within product receiving means such as the fingers or cassettes or auger flights towards an extraction station where the FMCG products can be removed from the stacker by an extraction device configured to remove at least one FMCG product from the stacker into a temporary storage device and at a later moment in time, re-feed products stored in the temporary storage device back into either the original stacker or a new secondary stacker system.

The stacker may be a vertical stacker, or at any angle between vertical and horizontal. Optionally, the angle is selected to at least partially compensate for the continuous rotation of the stacker. The angle may be between 0 and 20 degrees.

In this method, the storage device may be capable of storing from 1 to 10 000 products between 1 millisecond to 10 years and may have between 1-1000 chambers with each chamber capable of holding between 1-1000 products.

The storage device useful in this method may move in an orientation other than the orientation of the product flow to allow products to be inserted and stored in more than 1 chamber. The storage device may move in an orientation similar to the orientation of the product flow into a phased position with the product flow to allow re-ordered products to be inserted into defined locations within the storage device.

The present invention also relates to a method for producing customized FMCG products comprising of one or more of the following steps:

1—The design and acquisition of design related data for the specific customized product(s), typically via Internet connected system such as desktop PC, laptop, mobile device such as IPhone, Android, or tablet device.

2—Analysis of acquired data and rejecting any orders that do not conform to brand/companies code of practise.

3—Conversion of customized data into a suitable format ready for actual production.

4—Raw Material(s) customization and/or component and/or sub assembly production according to customizer's design.

5—The in-feed of material(s) and/or assemblies outlined in (4) in to the production process at a higher speed to the processes outlined in (4).

6—Buffer/storage of any orders which are not 100% correctly fulfilled and the re-order of any missing products/items.

7—Buffer/storage of customized products that would feed in at a later date to non-customized products.

8—The combined of partially filled orders with re-ordered products/items and subsequent re-feed back into the production process.

9—Linking of shipment address to product.

10—Shipment of customized products to shipment address.

Further, the present invention also relates to a method for producing customized FMCG products comprising of one or more of the following steps:

1—The design and acquisition of design related data for the specific customized product(s), typically via Internet connected system such as desktop PC, laptop, mobile device such as IPhone, Android, or tablet device.

2—Analysis of acquired data and rejecting any orders that do not conform to brand/companies code of practise.

3—Conversion of customized data into a suitable format ready for actual production.

4—Buffer/storage of any orders which are not 100% correctly fulfilled and the re-order of any missing products/items.

5—Buffer/storage of customized products that would feed in at a later date to non-customized products.

6—The combined of partially filled orders with re-ordered products/items and subsequent re-feed back into the production process.

7—Linking of shipment address to product.

8—Shipment of customized products to shipment address.

A useful web delivery device such as a splicer or defestooning system may be capable to deliver both a customized web and a non-customized web to a FMCG web based production process. The webs widths between the customized web and a non-customize web may have a width variance of less than 1000 mm. The web basis weight variations between the customized web and a non-customized web may have a gram per square meter (g/m$^2$) variance of less than 1000 g/m$^2$.

The equipment for the manufacturing method may comprise an automatic or semi-automatic splice process where the associated splicer box has one out-feed web and three or more in-feed webs, and one or more of the in-feed webs is/are a customized web(s). Optionally, the out-feed web is phased.

A web delivery device useful in the present manufacturing process such as a splicer supplying a single out-feed stream of material may have 3 or more unwinding systems (mandrills) where at least one of the mandrills operates in both a clockwise & anticlockwise direction. Optionally, the out-feed web is phased.

The manufacturing method may further comprise an automatic splice preparation method where a customized web is placed semi automatically or automatically into a splice box system after web customization cycle has been completed. Optionally, the out-feed web is phased.

The present invention also relates to an integrated FMCG web based production process consisting of a secondary or side stream production process that can be carried out independently of the main stream production process that is used to produce components or assemblies of the main process that is thereafter re-fed into the main production process.

The integrated FMCG web based production process may comprise a multiple side stream production process that can be carried out independently of the main production process that is used to produce components or assemblies of the main process that is thereafter re-fed into the main production process.

The integrated FMCG web based production process may comprise a secondary production process that can be carried out independently of the main production process that may be used to produce components or assemblies of the main process at a web speed to the main production process that is thereafter re-fed into the main production process.

The integrated FMCG web based production process may comprise a multiple production process that can be carried out independently of the main production process that may be used to produce components or assemblies of the main process at a web speed to the main production process that is thereafter re-fed into the main production process.

In the method for producing customized products with multiple printed features on a web based FMCG production line the printed features may be re-fed back into the production system in synchronisation with each other. The customized printed features may be applied on a multitude of webs on a web based FMCG production line where the printed features are at a later date re-fed back into the production system in synchronisation with each other.

The integrated FMCG production system may be connected directly to the Internet or indirectly to the Internet or indirectly to the Internet via a central command/management system that can receive customized production data to enable the production of customized products.

In another aspect, the present invention relates to a network of FMCG production systems comprising more than one FMCG production system connected directly to the Internet or indirectly to the Internet or indirectly to the Internet via a central command/management system which has the capability to send customized product designs to a specific production system, the decision hereof based on data enclosed in the customizers design requirements which can include but is not limited to product size, product features, product artwork, product additions and can also include customizer location and FMCG production system location. The central command/management system may include a database of article information, e.g. clothing articles information, including size and shape related data which can be referenced by the software to enable product sizing selection to take place, and/or a database of human body size information including size and shape related data which can be referenced by the software to enable product sizing selection to take place.

Such a FMCG production process connected directly to the Internet or indirectly to the Internet or indirectly to the Internet via a central command/management system may be capable to produce customized products where the in-feed/metering speeds of one or more raw materials being used in the product can be adjusted according to the customizer's design requirements.

In such a web based FMCG customization process, the customizers can enter their customized designs in 2D format or partial 2D format or in a 3D format whereby a 3D image is displayed of the customized design giving the customizer a visual image of either a complete or partially complete image of their customized design(s) whereby this image is either constantly updated, or updated at defined periods in time, or updated after a refresh command is used.

Such a FMCG production process may have the capability to produce customized products where the customized design data is acquired and/or sent in an original or a modified format to an inspection quality control process where this data can be used to inspect customized products produced.

The customized products may be inspected whereby a customized product design is sent to a vision system inspecting the customized products on-line or off-line where the vision system compares the finished product to the customized design and has the capability to reject any products which do not confirm to the customized design.

A FMCG production process may have the capability to produce customized products having the capability, either automatically or semi automatically, or manually, to re-order missing orders should an order not be fulfilled during the initial and any subsequent production runs.

In a FMCG web based production process, one or more webs may have been customized where the customized web includes an identification system enclosed on or within the customized webs which can be used to synchronise customized webs with each other should one or more webs become de-synchronised, wherein an identifier as a visual and/or machine-recognizable identification is used, which may be made up of one or more of the following: colours, numbers, alphabet letters, symbols, barcodes, QR Codes, RFID tags, electronic signals, magnetic strips or chemicals.

Such a method may be applicable for a hygienic product such as a diaper wherein the identifier is located either behind the interface between tapes and back-sheet, or the tapes and ears, or the ears and back-sheet or the frontal tape and back-sheet. Such a method may also be applicable for a rolled product such as toilet roll or kitchen roll wherein the identifier is located on the inner surface of the roll or within 1000 mm of the leading edge glue strip.

In yet a further aspect, the present invention relates to a web based production process where one or more webs have been customized where the customized web include an identification enclosed on or within the customized webs which can be used to synchronise customized webs with each other should a failure mode occur during production and webs become de-synchronised. The identifier may be a visual and/or machine-recognizable identification, such as by being selected from the group consisting of colours, numbers, alphabet letters, symbols, barcodes, QR Codes, RFID tags, electronic signals, magnetic strips or chemicals.

Such a method may be applicable for a hygienic product such as a diaper, wherein the identifier is located either behind the interface between tapes and back-sheet, or the tapes and ears, or the ears and back-sheet or the frontal tape and back-sheet.

Such a method may also be applicable for a rolled product such as toilet roll or kitchen roll wherein the identifier is located on the inner surface of the roll or within 1000 mm of the leading edge glue strip.

Such an identification system outlined on the one or more customized webs can be used by the production system in the event that the synchronise web(s) have become de-synchronised, either being automatically or manually entered into the production system to allow the production system to synchronise itself with the phased customized product, wherein the identifier may be a visual and/or machine-recognizable identification. The identifier may be selected from the group consisting of colours, numbers, alphabet letters, symbols, barcodes, QR Codes, RFID tags, electronic signals, magnetic strips or chemicals.

This method can be applied for a hygienic product such as a diaper wherein the identifier is located either behind the interface between tapes and back-sheet, or the tapes and ears, or the ears and back-sheet or the frontal tape and back-sheet. This method can be applied for a rolled product such as toilet roll or kitchen roll wherein the identifier is located on the inner surface of the roll or within 1000 mm of the leading edge glue strip.

In yet another aspect, the present invention relates to a method for producing FMGC products, which are a series of individual products or of products being connected along a web, which are travelling with a main stream production process speed. They comprise repeating or non-repeating features resulting from applying or not-applying process steps that are either discrete steps or are executed as continuously varying but phased process conditions, whereby the process steps are selected from the group consisting of mechanically or thermally treating the product,
adding visual indicia, preferably by ink printing,
adding further components, webs or web-pieces, or sub-assemblies, optionally resulting from a side stream process at a differing side stream process speed;

The process further comprises the steps of
applying an identifier to each of the product or the further components, webs or web-pieces, or sub-assemblies prior to being applied to the products, the identifier being the connection or nexus of the product or the further components, webs or web-pieces, or sub-assemblies and the respective features;
executing a quality control step, preferably an automatic visual inspection, on the product or the further components, webs or web-pieces, or sub-assemblies prior or after addition to the product;
monitoring defect or out-of phase products or further components, webs or web-pieces, or sub-assemblies;
removing the defect or out of phase products or further components, webs or web-pieces, or sub-assemblies from the respective process whilst continuing the processing of other products or further components, webs or web-pieces, or sub-assemblies;
monitoring the identifier of the further components, webs or web-pieces, or sub-assemblies;
adjusting the process settings such that the respective features are applied at a predetermined positioning to the product or the further components, webs or web-pieces, or sub-assemblies are combined with the respective features according to the identifier.

The adjusting of the process settings comprises one or more steps selected from the group consisting of
temporarily or permanently adjusting the main stream production process speed;
temporarily or permanently adjusting the side stream production process speed;
adjusting the cut length of pieces of webs by cutting and removal of web material or by splicing and adding web material of the same or different type.

Optionally, it may further comprise the step of collating a predetermined number of products satisfying predetermined quality control criteria, optionally by temporarily storing such products in a side stream storage.

In yet another aspect, the present invention further relates to a method for synchronising a non-synchronised FMCG production system having a single customized web or component stream either manually or semi automatically or automatically by determining the phasing of customized FMCG product components used within the FMCG product and may comprise the steps of:

A—Applying an identifier to a customized FMCG product or group of products or one or more components or artwork or web or webs or sub-assemblies of the FMCG product or products to enable the identification of the customized FMCG product or group of products or one or more components or artwork or web or webs or sub-assemblies of the FMCG product or products after the identifier has been applied.

B—Reading the identifier manually or semi automatically or automatically at a defined location in the production process.

C—Feeding information contained within the identifier into the system controlling the production process.

D—The synchronisation of the production system to the identifier.

The identifier may be a visual and/or machine-recognizable identification, optionally selected from the group consisting of colours, numbers, alphabet letters, symbols, barcodes, QR Codes, RFID tags, electronic signals, magnetic strips or chemicals.

This method may be applicable for a hygienic product such as a diaper wherein the identifier is located either behind the interface between tapes and back-sheet, or the tapes and ears, or the ears and back-sheet or the frontal tape and back-sheet.

This method may be applicable for a rolled product such as toilet roll or kitchen roll wherein the identifier is located on the inner surface of the roll or within 1000 mm of the leading edge glue strip.

The present invention further relates to a method for synchronising a non-synchronised FMCG production system having a multiple customized webs or component streams either manually or semi automatically or automatically by determining the phasing of customized FMCG product components used within the FMCG product comprising the steps of:

A—Applying an identifier to a customized FMCG product or group of products or one or more components or artwork or web or webs or sub-assemblies of the FMCG product or products to enable the identification of the customized FMCG product or group of products or one or more components or artwork or web or webs or sub-assemblies of the FMCG product or products after the identifier has been applied.

B—Re-threading if applicable any damaged materials back into the production system up to a point where no further damage has occurred.

C—Reading the identifiers manually or semi automatically or automatically at a defined locations in the production process.

C—Feeding information contained within the identifiers into the production process.

D—The calculation of which webs are out of phase and the distance by which the web needs to be extended in order to become synchronised.

E—The adding of a temporary material to the web(s) which need extending.

F—The movement of the production process of a defined position to pull the product webs including the web with the extension material attached into the production system to enable all webs to become synchronised.

G—The removal of the temporary material and the re-splicing of the customized web.

H—The synchronisation of the production system to the identifier.

E—The re-synchronisation of other parts of the FMCG product or group of products or one or more components or artwork or web or webs or sub-assemblies and or customized component to same standard identifier associate.

The identifier may be a visual and/or machine-recognizable identification, optionally selected from the group consisting of colours, numbers, alphabet letters, symbols, barcodes, QR Codes, RFID tags, electronic signals, magnetic strips of chemicals.

This method may be applicable for a hygienic product such as a diaper wherein the identifier is located either behind the interface between tapes and back-sheet, or the tapes and ears, or the ears and back-sheet or the frontal tape and back-sheet.

This method may be applicable for a rolled product such as toilet roll or kitchen roll wherein the identifier is located on the inner surface of the roll or within 1000 mm of the leading edge glue strip. The present invention may relate to an integrated cleansing product or products, such as a tissue(s) or wipe(s) either wet or dry which is integrated into a hygienic product located between the top sheet and back sheet and which has the capability to be removed through either the top sheet or back sheet or between the top sheet or back sheet without rendering hygiene product unusable.

The method according to the present invention may comprise a pick & place process integrated into a FMCG web based production process, which further may be capable to insert an RFID tag into 1 or more products held within a bag or box, wherein further the bag and/or box also may have an RFID tag attached.

BRIEF DESCRIPTION OF THE DRAWINGS

Same numerals indicate same or equivalent features.

DESCRIPTION

Figure 1A:
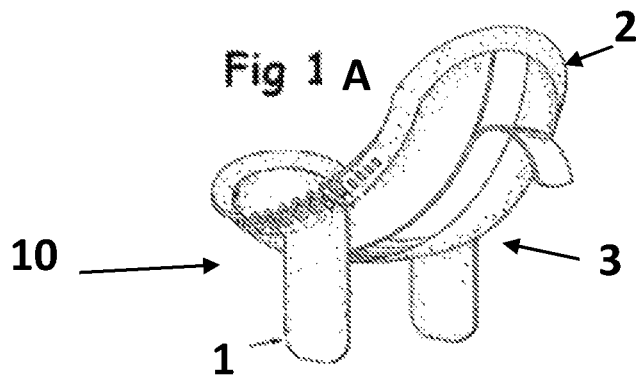
FIG. 1A is an outline of a feminine product showing customized artwork and coloration surfaces on various parts or portions of the product.
Figure 1B:
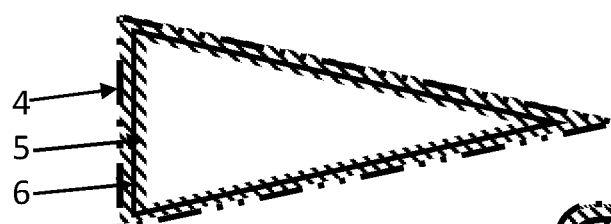
FIG. 1B to F outline various shape configurations of feminine hygiene products.
Figure 1C:
Figure 1D:
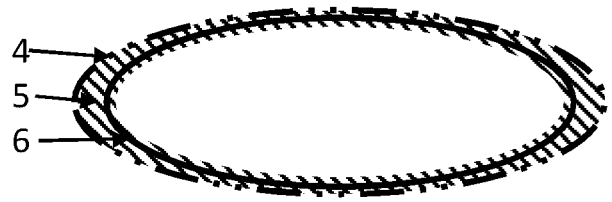
Figure 1E:
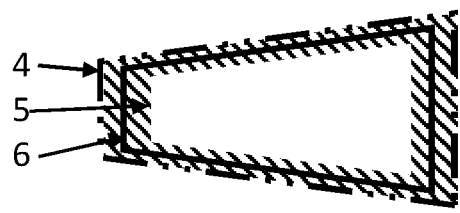
Figure 1F:
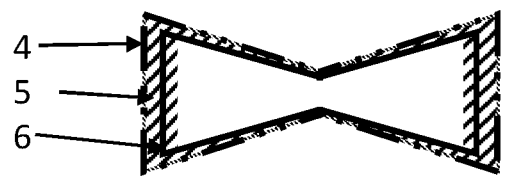

It is an object of the present invention to provide a new production methodology and respective systems which enable customized products to be made on a high-speed production process either as a dedicated process or in conjunction with on-going standard SKU production at a lower production speed and later fed into the original production system at standard production speeds or at a speed faster than the customization production process. As the percentage of customized production is expected to be a relatively small percentage of overall production volume, in most instances, it is preferred that the customized production is be carried out on existing high-speed production process in parallel to standard production rather than operating a dedicated production asset solely for customized production. Furthermore, having dedicated large scale customized production system in a fixed location may often not be the best logistical approach as this would typically mean that the shipment distance between production process and consumer would be considerable. Having a larger number of lower capacity lower cost customized production systems located closer to the end-consumer would reduce environmental impact as transportation and respective emissions related to the transportation effort would be reduced.

In order to achieve a direct interface with the customer, hereinafter referred to as the "customizer", the existing product or brand's associated website could be upgraded respectively with the addition of a new website feature offering a new interface with the customizer, where individually customized products can be defined e.g. with the physical design, the physical interfaces of the customizer typically being either a desktop PC, or a laptop, or a mobile device such as a "smartphone" or "tablet". The associated website could offer a 2D interface where users can design their specific artwork image and insert personal items such as digital photos and other digital images or text or artwork, the website could also display a 3D rendered image, or partially rendered image showing the user how their finished customized product will look. As part of this customization process, specific user details such as body measures like weight, height or waist diameter could also be added to enhance the overall benefit and value of the customization process. The website could also have the capability to interface with a database of clothing and respective clothing sizes and other items related to the consumer. If for instance a lady wished to purchase a feminine protection product where the surface in contact with her body remained white and where any surfaces of the product visible to the outside of her undergarment could be coloured to the exact colour of her undergarment, by selecting the respective undergarment make and/or model and/or colour and/or product code would allow the ink to be printed in the exact colour in the exact locations required which would ultimately reduce ink usage and environmental impact. Via the connection of this system to a laser cutter or similar, the actual final shape of the product could also be shaped to fit her undergarment, and/or, the actual production line could be chosen to closest match here desired products size/shape/design. To achieve the overall customization capability throughout the supply chain, the manufacturing equipment requires additional systems, features and process steps to be installed and/or the modification of existing systems which includes but is not limited to the following:

(1) The modification of existing production processes to allow that the shape and/or size of the product can be customized via the defined metering of individual product components within the final product that would be produced according to the customizer's design and would require the linking of material metering systems (such as servo drives) to follow the customized design parameters (such as the tape length on a diaper);

(2) The modification of CD tracking and respective CD tracking of in-feed components;

(3) The addition of temporary storage systems to allow the temporary storage of incomplete orders until any missing products can be added to fulfil the order;

(4) The re-ordering capability to re-order missing products, merge newly ordered products with incomplete orders and send back into the production (bagging) process to complete the customizer's order;

(5) the addition of temporary storage systems to the hold customized products which can later be re-fed back into non-customized product streams to give the capability to produce partially customized shipments;

(6) the addition of new systems to achieve customization functionality such as on-line printing systems and pick & place systems to place and/or insert and/or attach additional products or components into the product(s).

The concept of "pick & place" systems could be a specifically designed pick and place system consisting of 1 or 2 or 3 or 4 or 5 or 6 or 7 or 8 or 9 or 10 axis system or a commercial system such as a 1 or 2 or 3 or 4 or 5 or 6 or 7 or 8 or 9 or 10 axis robot or similar. The pick & place process would have the capability to add additional items into or onto the FMCG products that could be either a single item or multiple items, and could include, but not limited to items such as an RFID tags and/or credit cards and/or items used for promotion purposes, or could be a consumable item such as a baby wet wipe or other product where the consumer could order say a 40 pack of diapers of which say 5 diapers in the total package would be travel diapers where an integrated wipe would be included within the product and where the travel diapers could also display the contact details of the family just in-case the baby would become departed from their family whilst away from home. During the ordering process, the customizer could not only—if desired—specify how many diapers in the bag would require an integrated wipe they could also for instance specify the type of lotion within the wipe (say scentless, aloe-vera, lavender, lemon grass etc.) and their specific artwork design if desired. As many of these pick & place systems available today are not capable to run at today's production speeds, with baby diaper systems for instance running between 200-3000 products per minute, the present invention provides a process to re-feed secondary assemblies produced at slower speeds back into the main stream production process at full line speed (or at a speed faster than the customization speed) once they have been assembled. Additional embodiments described herein relate to new systems to solve other technical challenges that exist once the customized products have been produced as the overall production system is required to manage the products after they have been produced to ensure they are correctly sorted, packaged, and the total customizer's order fulfilled which presents huge operational problems considering that the majority of today's high speed FMCG production lines also have automated product reject systems meaning there is a high chance that a customizer's order is not 100% fulfilled during the first production run. Assuming for instance that a batch of 20 diapers with customizer's specific artwork were successfully printed however during the automated assembly process, a splice existed on one of the raw material streams and e.g. 3 diapers were rejected, this would not only mean that the customizers would not receive their fulfilled order, but furthermore, the entire manufacturing system risks becoming out of synchronisation if the overall process is not managed correctly. Solutions to solve these problems are described herein that ultimately allow a high-speed manufacturing system to run at normal production speed without any significant change in the existing manual operational efforts. Once the customized product has been produced, the product is then packaged and labelled with the customizer's shipment address (or another body assigned by the customizer) as the product would most likely be shipped directly to the customizer or a body chosen by the customizer and as such, the respective shipment address would be added to the customized product for direct shipment.

In addition to the benefits of the customization as such are secondary benefits such as of enhanced consumer brand awareness that would significantly enhance sales of the standard non-customized FMCG products of the same brand through (i) the customization process itself, and/or (ii) dedicated marketing and branding campaigns that make dedicated use of the customization feature and/or (iii) enhanced customer awareness of the brand as a direct result of the customized products. Whilst some products such as liquid hair care and detergent products would most likely have limited customization use or benefit, other product categories such as absorption articles would have a higher benefit to the consumer and respective FMCG companies and brands selling such customized products. Feminine protection pads could for example be ordered according to the actual colour of the customizer's underwear and would give enhanced consumer satisfaction as today only a very small range of colours are available, (normal whitish, pink, black or blue) and typically with such products available today, the entire product is coloured where a customized product could to only the areas on the outer surface of the feminine pad where colour such as ink is required.

Such an example is shown in FIG. 1, with (1A) outlining a possible customization artwork colour surface on a feminine hygiene product (10) such as on the fold over tabs (1), customizing the perimeter around the product (2) which could be visible from outside of the garment to which the product would be attached with, or customizing the entire surface of the product which comes into contact with the garment (3). The possibility also exists to customize the shape of the final product via a flexible cutting system such as a laser, or plasma cutter or hot air cutter, hot surface, ultrasonic device or similar. In this scenario, the customizer would either customize the product themself or select the garment from an available database to which the customizer intends to attach the product once produced, with the database including such items as product shape, size, colour etc. Artwork surfaces are defined onto which the customizer can add their artwork should this be required. Once this stage in the ordering process is complete, it is very easy to assign this order to a specifically chosen production system that already is producing product of a similar shape and design to the customizer's desired design thereby reducing the amount of change processes required, and/or, the amount of raw material wastage as in such instances, a laser would cut the exact shape of the product according to the customizer's exact design requirements. FIG. 1B to 1F depict schematically examples of various shape profiles, with a standard non-customized product shape (solid line—6),
a crimp and/or glued area (dashed region—5) which could in some instances be wider than standard products, and which may be determined by customizer's requirements directly or by pre-selection in the production process, and
with an example of where the customized cut line (dash dotted line—4) could replace the standard cut line (6). Such a process would be able to produce the perfectly sized and shaped product for the actual garment to which it would be attached, with the fold-over tabs and other product features also being perfectly sized, which ultimately means that there would be an environmental benefit as plastic trim being removed from the original production process can easily be collected and recycled at the production site versus ending up as potential land fill.

Figure 2A:
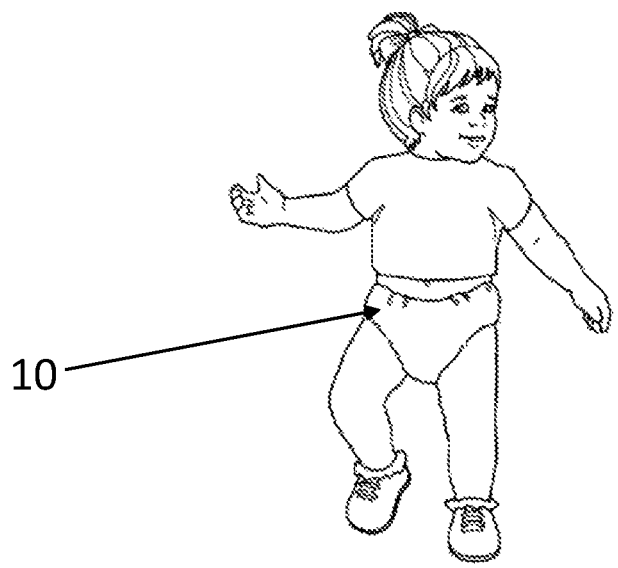
FIGS. 2A and B show an example of the customized surface of a baby diaper.
Figure 2B:
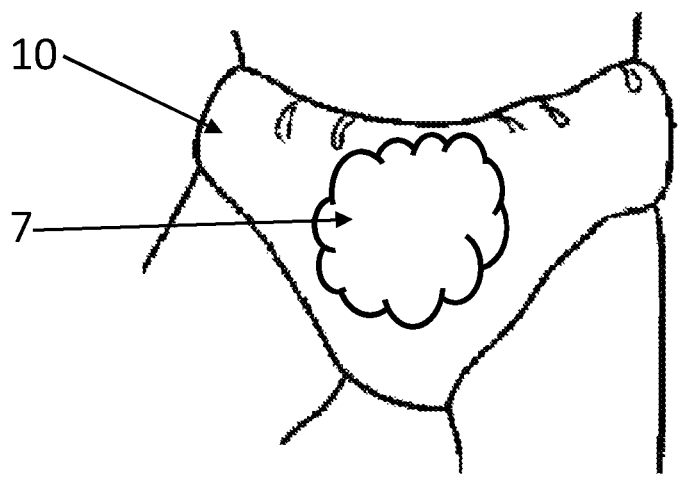

In relation to artwork design, essentially the entire FMCG product surface has the potential for customized artwork and/or coloration, however for some products, dedicated customized artwork surfaces could be defined. Whilst it can be applied to various products, the products discussed currently are shown in FIGS. 2A and B as customized diaper (10) with a customization surface (7), here shown in the front region of the article, though such a surface could be expanded to the rear and sides of the product and also could include other areas of the diaper including tapes, stretch zones and frontal tape. Exemplary uses for the customization may be as follows:

In case of baby diapers:
"My name is Max and I have lost my parents, please call my parents Mr. & Ms. Smith on +1234567 and tell them that you have found me";
"My name is Peter and I have lost my parents. We are on vacation and we are staying at the Beach Hotel, . . . ";
In case of adult incontinence care products for people of adult care homes:
"Dear Finder, my name is Joyce Williams, I am a patient at the xy Care Home and I am suffering from dementia and as such I am afraid I sometimes cannot remember my name and where I live. If you find me, and I am unable to find my way home, please call the xy Care Home on 123446, or call a Taxi to deliver me at the address . . . Sincerely yours Joyce";
Products could also be customized under the "fun" aspect, such as the following examples
"To my dearest husband Luke: If you are close enough to the diaper to read this message and you also experience a bad smell, THEN IT'S YOUR TURN TO CHANGE THE DIAPER! Your dearest wife Jane."
"Made with tender loving care";
"My name is Max, 1.2 kg and still growing",
"Dear grandson, you took three years to be conceived . . . Your parents finally succeeded!!"
"Does this diaper make my butt look big??"

Figure 3:
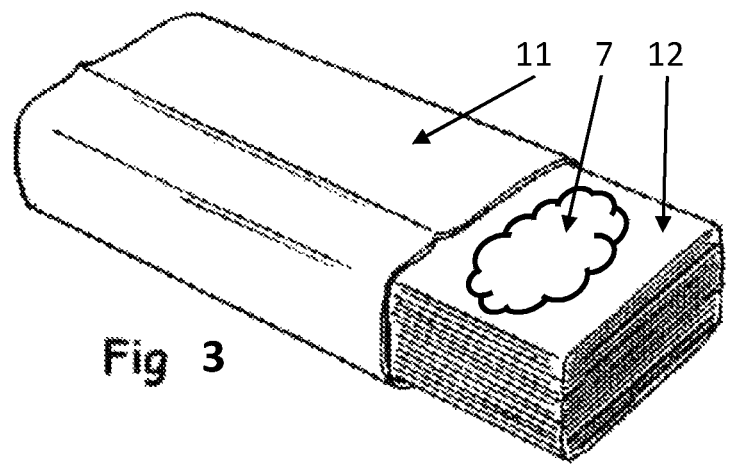
FIG. 3 shows an example of the customized surface of a tissue product.
Figure 16:
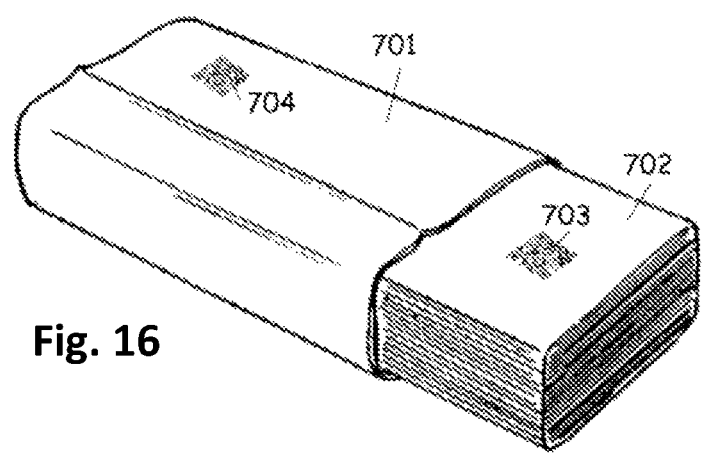
FIG. 16 depicts a customized folder product, such as tissues or wet wipes.

Also tissue packs could for instance have artwork related to the users specific fashion design preferences as shown in FIG. 3 depicting tissues (12) with a customized print region (7) inside a pack (11), such that if for instance the consumer is wearing a particularly styled and coloured outfit, the tissue design could match the design and colour of the wearer's outfit and in some instances, could be combined with a variety of brand marketing campaigns and/or in conjunction with a clothing manufacturer's brand marketing campaign or promotional event. Similarly, FIG. 16 depicts a customized folded product (702), such as tissues or wet wipes as may be made from be tissue or non-woven, in an outer containment material (701) which could be a wrapper material such as film/plastic or a cardboard material or similar. A customized identifier (703) may be attached to the folded product as well as to the outer containment material (704).

Figure 4:
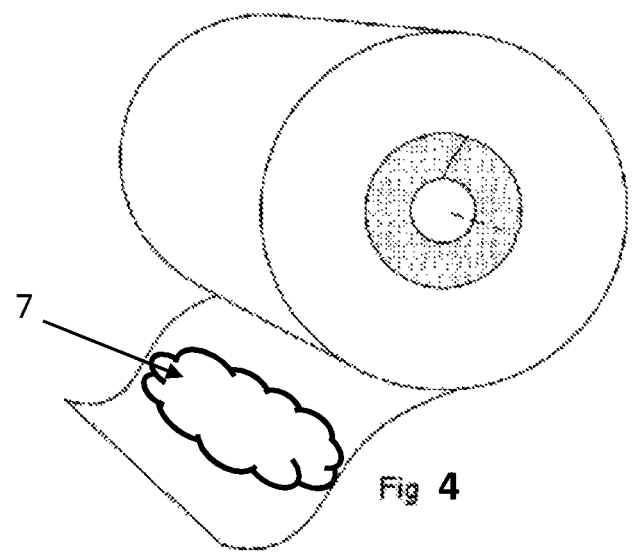
FIG. 4 shows an example of the customized surface of a toiletry product.
Figure 15:
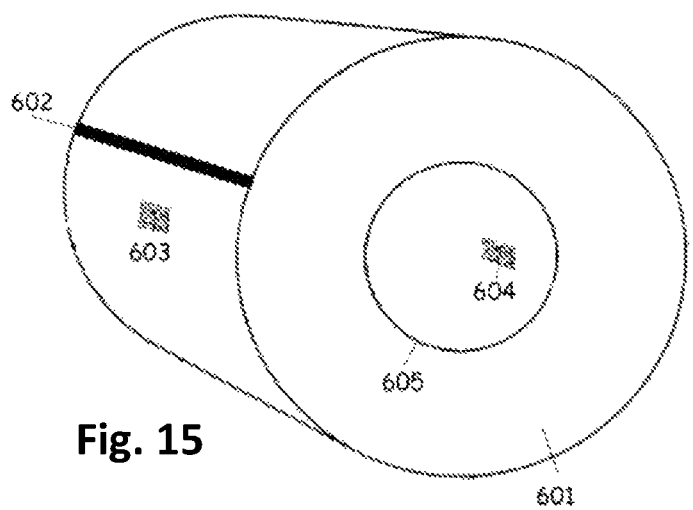
FIG. 15 depicts a customized rolled product such as kitchen or toilet paper.

Even products such as toilet rolls could for instance also have customizer's artwork as shown in FIG. 4, which could be of use to hotels. Similarly, as depicted in FIG. 15, a customized rolled product (601) such as kitchen or toilet paper as wound onto a core (605), comprising a glued section (602) that glues the leading edge back to the rolled material itself to prevent the roll from unwinding and a customized identifier (603) attached to the rolled product (601) as well as to the core (604).

Figure 5:
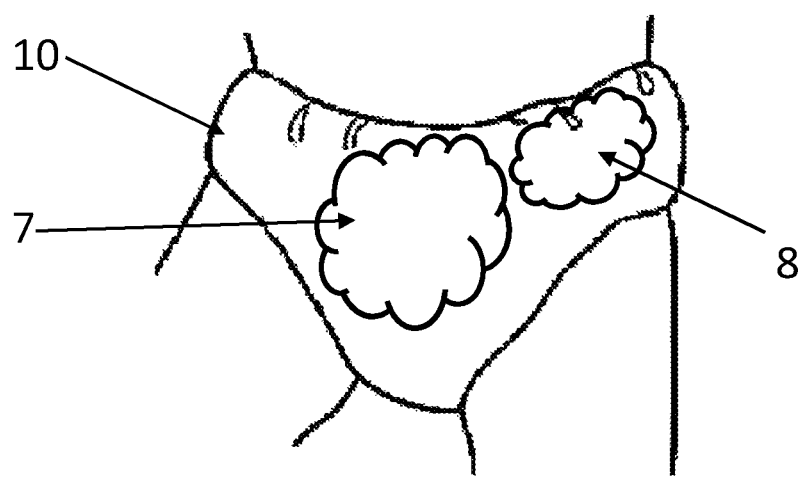
FIG. 5 shows a further example of customized surfaces of a baby diaper.
Figure 6A:
FIG. 6A shows an example of the customized surface of a face mask/beauty product.
Figure 6B:
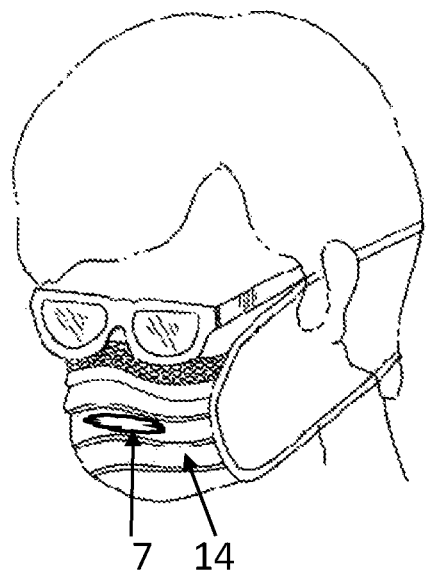
FIG. 6B shows an example of the customized surface of a breathing mask.
Figure 6C:
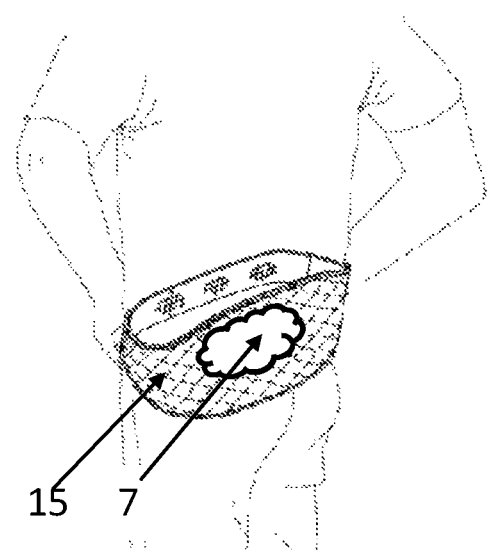
FIG. 6C shows an example of the customized surface of a back warmer—healthcare.
Figure 7:
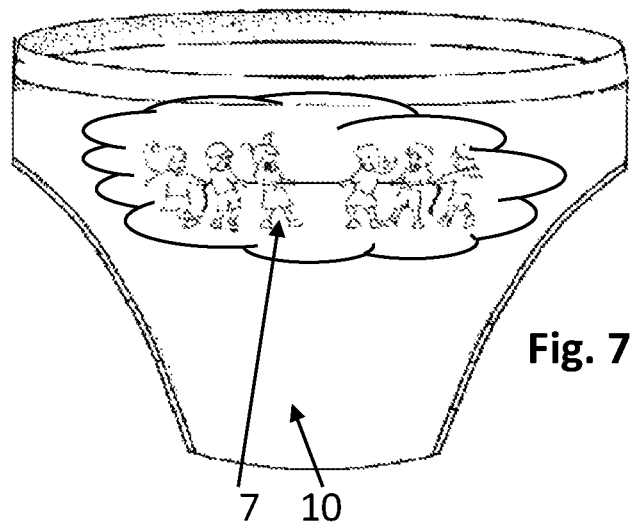
FIG. 7 shows an example of the customized surface of a baby diaper—artwork competition.

Having this new low cost customization capability also opens up new branding campaign options, not only for the original FMCG brand but also co-working with other brands operating in other completely different market segments. Hotels or any vacation of leisure venue could for instance offer a hotel branded product for guests for instance that require an unexpected diaper as shown in FIG. 5, with a first customization region (7), as may refer to the respective provider of the article, and a further customization region (8), as may refer to the manufacturer of the article. Also, certain events such as outdoor event of a company selling luxury off-road cars, could for instance as part of their annual outdoor marketing event offer a branded diaper as part of the overall event marketing materials and presents. Football clubs could easily make customized products for a particular venue, event or location. Luxury spas could for instance customize a facemask with their corporate branding, see FIG. 6A, and similar concepts could be used with breathable face-masks, see e.g. FIG. 6B. Health/medical organisations, could for instance brand a thermal care product with their corporate branding, see e.g. FIG. 6C. The system also opens up a platform for artwork competitions for schools and other events such as shown in FIG. 7, showing a customized region (7) on an absorbent article. Through the creation of joint marketing campaigns FMCGs can increase brand awareness and adopt dedicated marketing campaigns.

Figure 8:
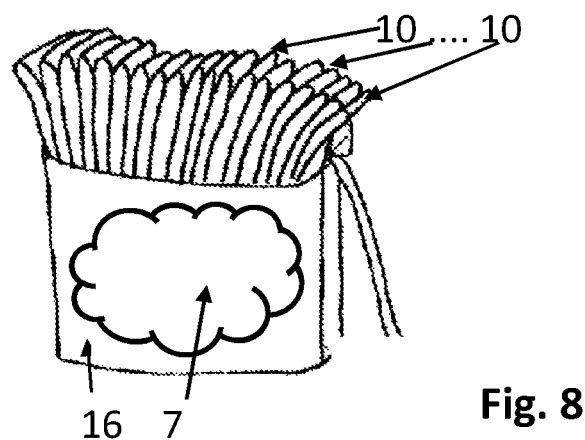
FIG. 8 shows an example of the customized surface of a baby diaper outer bag that has been sized according to the actual wearers body dimensions.

Customization would not only be limited to the products within the box or bag, customization can also be applied to the outer surface of the box/bag as shown in FIG. 8, with articles (10) such as diapers in a packing bag (16) with a customization region (7), where the customization of the article is based on users actual body weight and dimensions from which the correct product size is determined for the user. As a further part of the customization process, the outer packaging is printed accordingly to show that the products are of appropriate size for the user showing the users name and/or a digital image of the user that was also used in the artwork design of the customized products inside.

Figure 9:
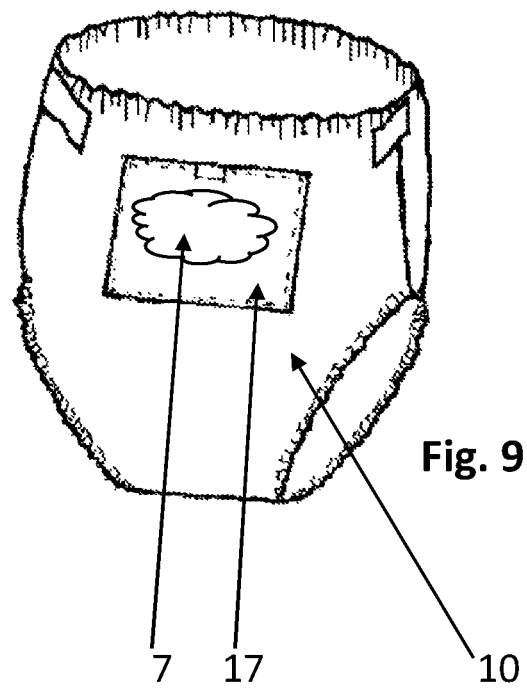
FIG. 9 shows an example of the customized surface of a baby diaper upon which a wet wipe has been attached.

FIG. 9 depicts schematically an example of the customized surface of an article (10), such as a baby diaper, upon which a wet wipe inside a package (17) is attached, though this could also be placed inside the diaper. The customizer could for instance choose to have wet wipes or other products combined with the diaper, for instance in case the customizer requires travel diapers or similar where having combined wet wipes could be advantageous to the user. The customization area (7) could be chosen as part of the customization process, or the desired type of wipe. For travel diapers for instance, if the customizer were traveling away from home and were aware that a requirement of say 5 travel diapers were required, a total of 40 diapers could be ordered of which 5 could be travel diapers consisting of in integrated wipe and respective artwork. Also, the combined packaging may comprise diapers with varying absorbency, such as a night diaper with an increased absorbency, such as by having a higher amount of superabsorbent material, compared to diapers for daytime use. A customizer may also wish to have differently scented diapers, such as having sleep promoting smells, such as lavender, for night diapers and refreshing smells like eucalyptus or grapefruit for day diapers. Similarly, articles may be adapted in a reaction to certain skin conditions, such as certain customized articles comprising selected skin creams or lotion, and other articles comprise different or no lotion or cream. Certain diapers in a pack may also comprise test strips, patches or QR codes that could signal bodily disorders, or may include electronic patches that may transmit signals wirelessly to a caretaker.

Thus, in one aspect, the present invention is a manufacturing process as a combination of multiple steps combined so as to allow the automatic or semi-automatic manufacture of customized products and is outlined as follows.

The Customization Processes and Respective Equipment

Figure 10:
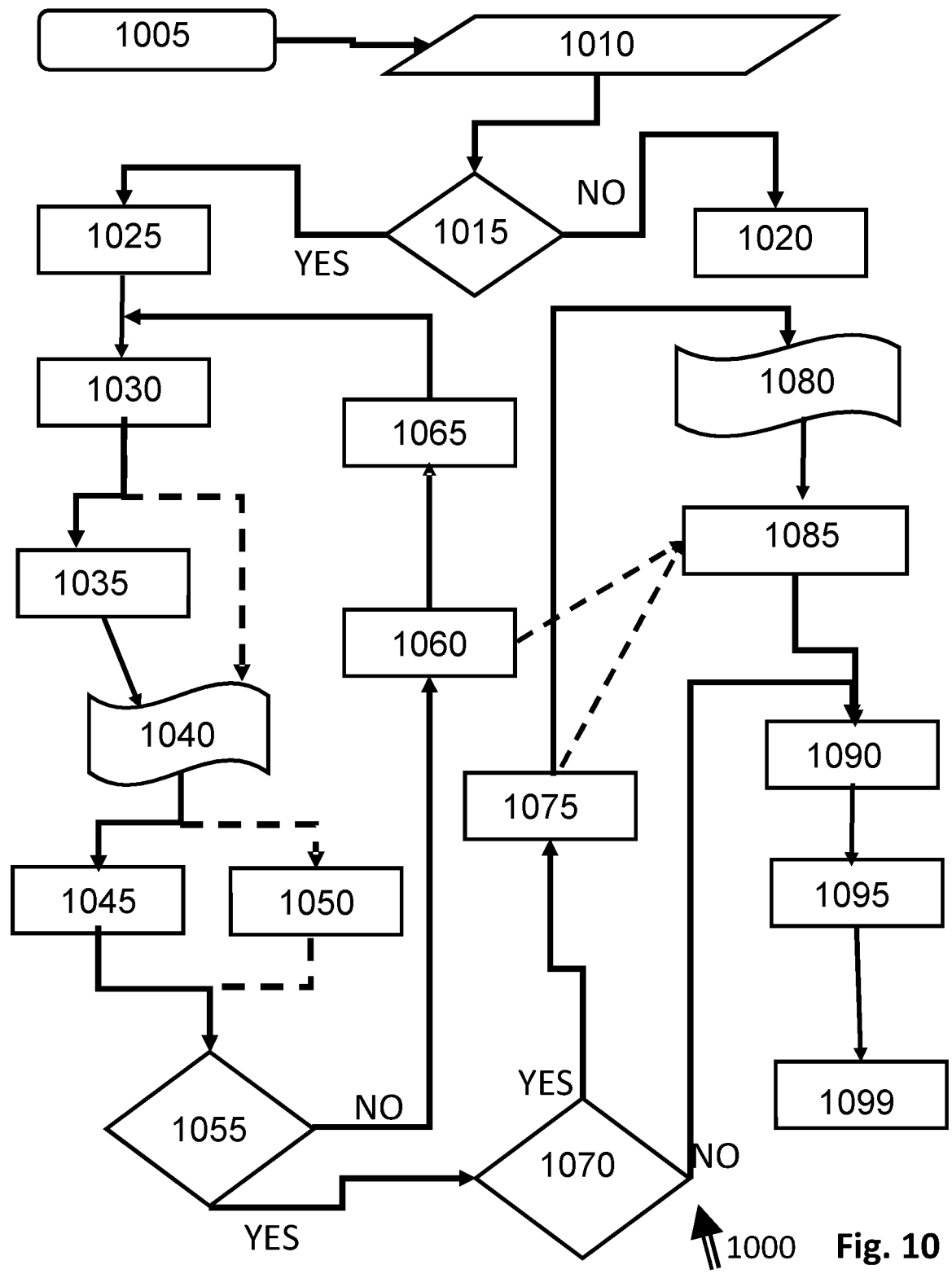
FIG. 10 is a flow chart of the customization process.

Without any intended limitation, the principle for a process of customization and the respective equipment elements are now explained first in an overview followed by a more detailed description by referring to the process flow chart of FIG. 10. Thus a process (1000) according to the present invention may comprise the following steps:

1005—A customer as a potential customizer connects to the website or a similar interface of the manufacturer using electronic devices.

1010—The customizer provides the name, delivery address, payment details to the manufacturer's system and makes desired product selection(s), such as desired size, colour but also particular feature options and/or artwork, optionally providing self-designed artwork elements.

1015—The manufacturer's system performs an analysis of acquired data, rejecting and cancelling ("NO"— 1020) any orders that do not conform to manufacturer's criteria such as brand/company/website's code of practise. The "good" orders ("YES") are further processed, for the "bad ones ("NO"), a rejection note may be sent out.

1025—The customizer's data, especially address, sizing as well as particular features are compared to most compatible production system as well as production facility.

1030—These data are converted into a suitable format required for the manufacturing process.

Based on these data, preferably by the automated system or with an interaction of the operator, it will be decided, if the customization will be execution in course of side stream production process (see steps 1035, 1040, 1045) or in a mainstream production process (see steps 1040, 1050, respectively), or a hybrid option, with all options continuing with step 1055.

Side Stream Option

1035—The specific raw materials and/or sub-assemblies are provided adequately according to customizer's requirements, whilst "standard" materials are delivered and used in the main stream production for "standard" product.

1040—Whilst the main stream production process manufactures "standard" product, the assembly process for the customized products is put on hold until all raw materials and sub-assemblies are ready to use.

1045—Then, the customization process step puts the "standard" materials or sub-assemblies on hold, and uses the dedicated materials or subassemblies to manufacture the customized product.

Main Stream Option

1040—At a predetermined time, the main stream production process is modified by a change in an process step or an additional process step, such as by changing the printing design, or adding a printing . . . .

1050— . . . thereby producing the customized product

The hybrid option comprised both options, namely the use of particular raw materials and/or sub-assemblies combined with further customization in the main stream.

1055—For all options, the products undergo a quality control check, counting on-target customized products, deciding if the predetermined number of customized products has not yet been completed, e.g. by rejects, ("NO" towards process step 1060) or "YES" to process step 1070.

1060—In case that the predetermined number of customized products has not yet been completed (e.g. by rejects), the system . . . .

1065— . . . loops back information and production requests, e.g to step 1030.

1070—In case the correct number of OK products has been produced it is established, if this has been established in an interrupted series ("YES" 4 process step 1075) or in single continuous series ("NO" 4 process step 1090).

1075—If the predetermined number for the order is not satisfied, the incomplete order is placed into a temporary storage system, which is further filled as appropriate products arrive.

1080—Depending on the predetermined pattern, a suitable point in time, e.g. a production interruption, is awaited . . . .

1085— . . . until these can be pulled from the temporary storage system.

1090—In either case, a full set of predetermined numbers of customized products is forwarded to the packing station.

1095—The full set of customized products is packed, optionally further customized such as by printing on the package, and connected to the customizer, such as by applying the address.

1099—The package may then be dispatched to the customizer.

Within this general set up, options and shortcuts may arise, such as, but without limitation selected from the groups of process steps consisting of:

Feeding material(s) and/or assemblies outlined in step (1035) to the production process at a higher speed than the process speed outlined in step (1030).

Storing customized products that would feed in at a later date to non-customized products.

Combining of partially filled orders with re-ordered products/items and the subsequent re-feed back into the manufacturing process for packaging and secondary packaging if applicable.

In the following, the individual process steps and/or options are described in more detail, also referring to FIG. 10.

1005—Potential Customizer Connecting to Customizing Website

As the first step in the process (1005), the customizer would typically log onto a website, which could be part of an existing brands or company's website or a dedicated website such as www.designyourowndiaperss.com or www.colourmypad.com and could be accessed using any present or future electronic device or any current electronic device such as desktop PC, laptop, mobile device such as smartphone, or tablet device.

1010—Data Input of Customizer

Figure 11:
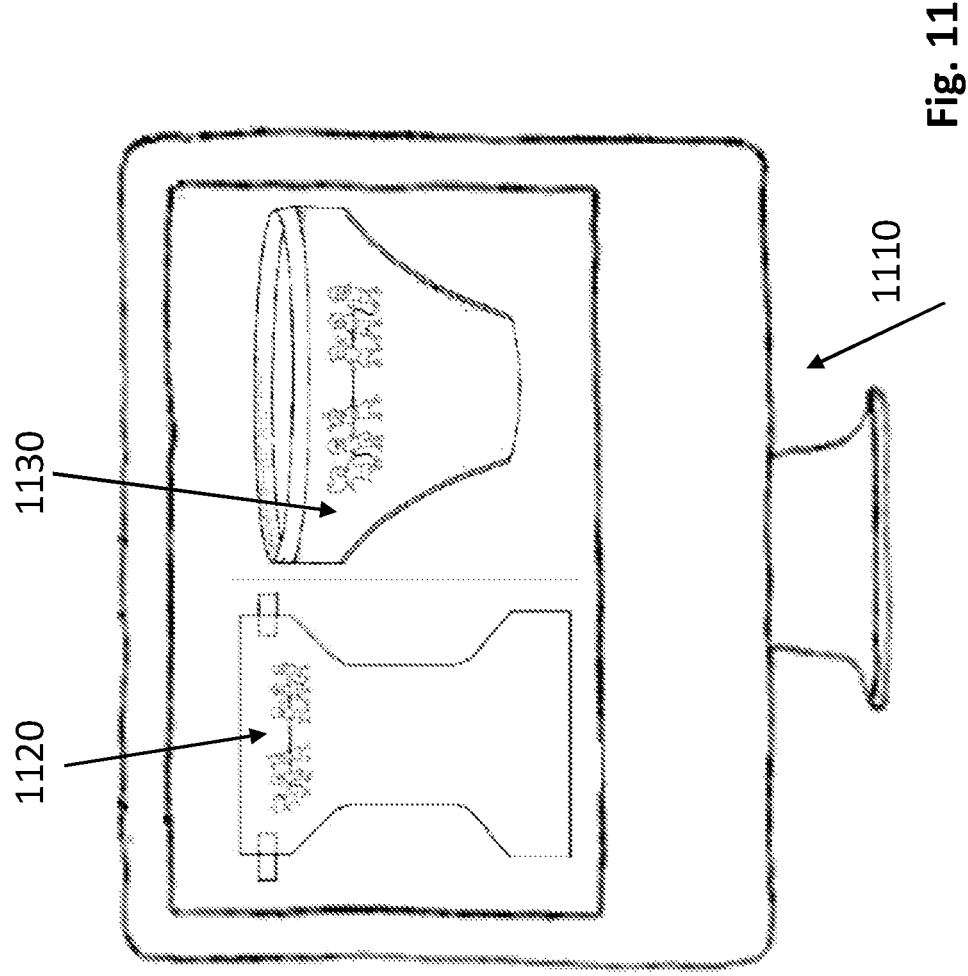
FIG. 11 is an outline of the website interface.

Once on the website, consumers would typically enter their client specific information, such as their name, shipment address, payment details and then specify the product and quantity they require (1010). Product size could be selected as per the standard sizes descriptions such as small, medium, larger, however for products such as diapers, a more intelligent interface could be provided where the customizer enters waist diameter and body weight and the software makes the best size selection based on this data. Additional optional extras can be selected such as the addition of RFID devices and medical or sensing devices and even items such as credit cards or similar object(s) could be attached or combined. Specific product sizes could be ordered as are available in the supermarket, however features on the product could also be customized such as fastening tape length specified according to customizer's requests. The customizer could also select a variety of colour options for either a single or multiple materials and also select options to design specific artwork on these materials. For a baby diaper for instance, artwork design surfaces could be on the back sheet area however artwork design surfaces could also be selected to be applied to additional such as elastic features, frontal tapes and fastening feature materials. As schematically indicated in FIG. 11, the associated website could offer a 2D interface (1120) where customizers can design their specific artwork image and insert dedicated items such as photos and other digital images, and/or a 3D rendered image (1130) showing the customizer how their finished customized product will look. The 3D image could be a fully rendered image, or a partial or low definition rendered image to reduce respective processing requirements data transfer requirements across the Internet. The rendered image could be automatically upgraded on a real time basis according to changes made in the 2D design area, or, the rendered image could be updated after a set time period, say every 30 seconds, or, the rendered image could be updated on demand when a refresh button is pressed.

1015—Initial Analysis of Acquired Data.

To avoid misuse of the system and potential negative effects to the product brand, and/or the company producing the products, all customized data received may be scanned and any customized orders containing items such undesired orders, including pornography, political reference, swear words or slang or any items detrimental to company or brand would not be produced with the respective order being cancelled with the customizer being respectively informed (1120).

1025—Comparing customization data with most compatible production system and/or closest manufacturing site.

1030—Converting customizer's design and feature options into format ready for manufacture.

In some instances, the customization design could be sent to a single production system dedicated to customized production, however, in most cases, a central system would assign a suitable manufacturing asset/system on which the customized products would be produced. The data for these decision(s) is based on a variety of data including but not limited to (i) production asset/system capability in consideration to the customizer's product design,
(ii) production site location and customizer's desired shipment location,
(iii) availability of the production asset/system.

All screened data would then be electronically modified and converted into the format required by the manufacturing system which would in most cases include the addition of markers which are discussed herein below and aid the operational staff to track and re-thread materials should any problems occur during the manufacture of the customized product(s). Product pitches for artwork would be set up to correspond to the actual manufacturing process. For items where multiple data streams are required, such as artwork requests on multiple components, for instance a diaper having customized artwork design on back-sheet, landing zone stretch ears and tapes, the production data would be managed accordingly within the production system so the printing systems printing the specific components remained in phase with each other during the complex production process.

1035—Raw Material and Sub Assembly Production

In some instances, production would be carried out directly as part of the main production processes (see process step 1050 herein below). In such cases, printing processes such as inkjet printing would run at full production speed and items being applied to the product such as via a pick & place robot would also run at full production speed.

Figure 12:
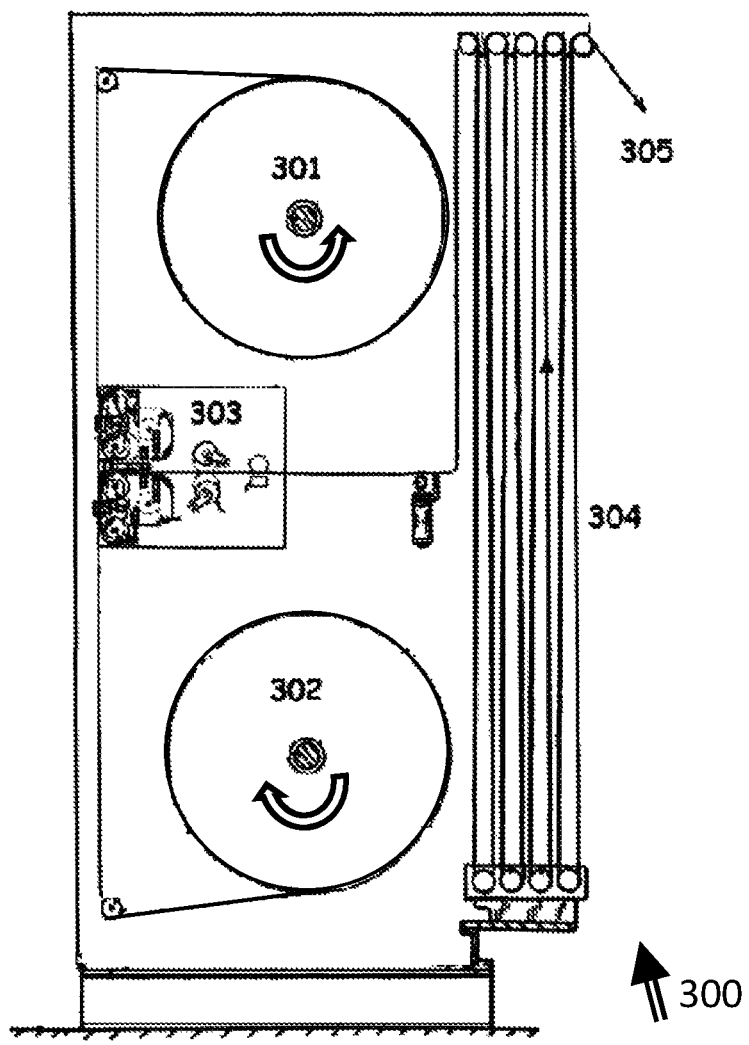
FIG. 12 depicts a standard raw material unwind stand in use with most web based FMCG production systems today.
Figure 13:
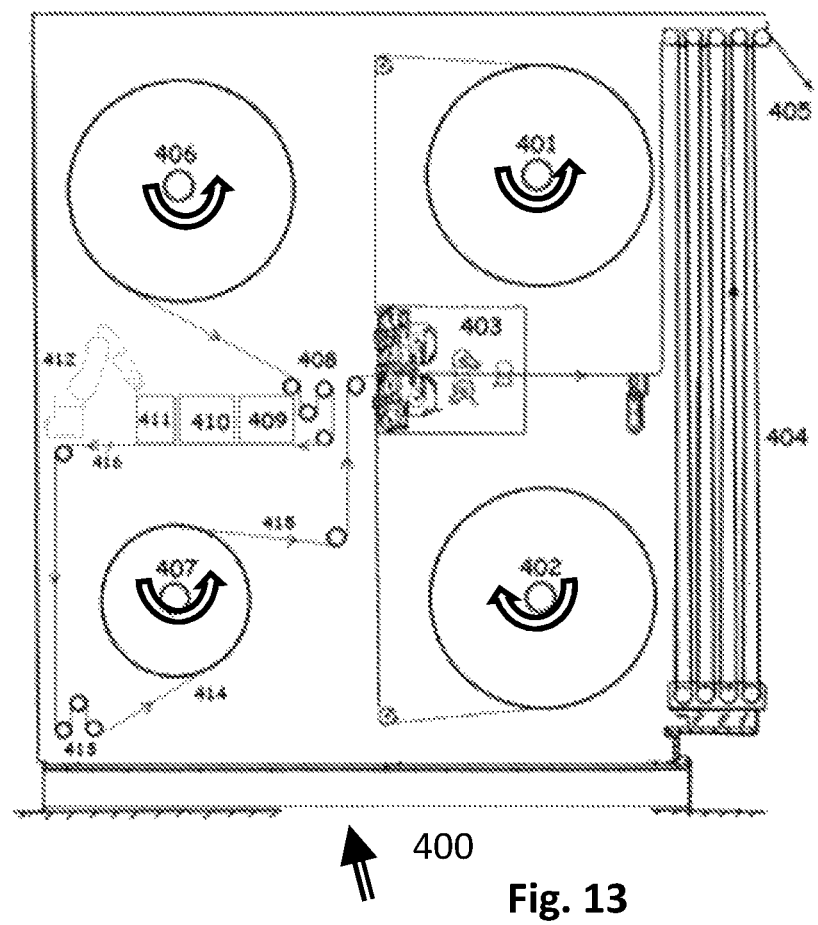
FIG. 13 depicts a customized raw material unwind stand which has additional web delivery systems attached particularly suitable for the present invention.

However, in the majority of cases, flexible processes capable of customization are not capable to run at production speeds typically associated with the high speed production of FMCGs. Furthermore, equipment such as high speed inkjet production process are very expensive and secondary high speed drying processes are required to dry the inks and in many cases, the inks required in such high speed processes are significantly more expensive then inks capable to run in slower speed processes and are more environmentally damaging. In such cases, such customization production work would be carried out in parallel to the main manufacturing process at a slower speed and later fed into the production system at full line speed at time of final product assembly/manufacture. In many instances, the raw materials used for customization production would have no prior artwork (would be white in most cases) and as such, overall ink usages levels could be lower than a non-customized production. For a diaper for example, the customized artwork would most likely be applied to a white back sheet, and in cases where artwork is applied to other diaper features, in these cases the raw materials would also usually be white. An example of such an apparatus is shown in FIG. 13 where a standard back sheet splicer is equipped with a secondary customization splicer utilising the same splicing mechanism such that it very suitably can be used for the present invention. Such an equipment is based on a conventional raw material unwind stand as can be seen in FIG. 12, as in use with most web based FMCG production systems today. A web material is unwound from a first (301) and a second (302) rotating mandrill, where either material being supplied from the first or second mandrill is transferred into a splice box (303) and thereafter to a buffering system (304) which ensures constant supply of material output (305) whilst in-feed speed changes during a splice change between 301 and 302.

Referring to FIG. 13 for the present application, standard first and second unwind mandrills (401, 402) together with a splice box (403) and buffering system (404) provide an out-feed (405) for a standard production back-sheet with standard artwork for the production system for making standard non-customized product. For incoming orders with customized artwork to be printed onto the backsheet, a white back sheet can be unwound from a plain material mandrill (406), printed in a printing equipment (409) and wound onto a customized material mandrill (407). The material may be transferred via a standard dancer system (408) to ensure web tension control and optionally via a web tracking device (not shown) to the printing equipment (409) may be any conventional printing system, such as inkjet or video jet or bubble jet or laser printer, optionally followed by an ink drying equipment (410). Additionally or alternatively a further component may be added to the web material in a sub component feeding system (411), or by a pick and place equipment, that may be custom made system or a commercial system, consisting of either 1 or 2 or 3 or 4 or 5 or 6 or 7 or 8 or 9 or 10 axis of motion (412) that applies these items onto the web being unwound from the plain material mandrill (406) at a predetermined position (416). Via a further dancer system (413) and optionally via a web tracking device (not shown) the web may be wound via material path (414) onto the customized material mandrill (407). Once the production of the customized material is complete on its roll, it can be unwound an unwinding path (415) into a splice system (403) which would feed in at full production speed into the manufacturing system via buffer (404) and out-feed (405). As this process is fully separated from the main production process at this stage in the customization process, this process can operate at a lower speed with lower cost printing equipment without the need to significant heating to dry the inks, which also reduced energy consumption. Further, the capacity of the system can be enhanced by adding an additional mandrill or mandrills that would allow the customization process to operate in parallel to finished customized rolls being unwound back into the production system.

1040—Awaiting Production Slot for the Customized Product

Thus, the customized material can now await a suitable slot in the manufacturing process, which can be determined automatically or by an interface with an operator.

1045—in Feed of Production Material in Production Process.

Once the customized material wound on customized material mandrill (407), the customized material can be fed into the main production process, e.g. via a splicer box (403) either manually or automatically. In the scenario where other customized processes are also in operation in the production system, such as printing processes on diaper tapes or frontal tapes, or RFID pick & place processes, these material streams would all be synchronised together to ensure the correct products were made according to the customizer's total design requirements. The synchronisation of the raw materials may also include the synchronisation of other components to be shipped to the customizer such as packaging materials or similar.

1050—Main Stream Process Customization

In the alternative to the side stream process customization or in addition thereto, the customized product may be made in the main stream process at main stream process speed, for example if the overall process speed is relatively low, or the printing ink is fast drying, or the applicator a high speed applicator. This may also be achieved by employing the technologies as described in U.S. Pat. No. 9,248,055, to which express reference is made, relating to a "on the fly size change" system allowing to adjust size of a diaper by automatic parameter input. Both for a main stream adjustment and for a side stream customization as described in the above, diapers may be customized with regard to absorbency by also adjusting the amount of superabsorbent material "on the fly", such as by adjusting scarfing, vacuum, speed or other process parameter in an otherwise well-known particle material printing process, such as generally described in EP1621165A1.

1055 Quality Check and "OK" Product Count

During the manufacture of the respective customized products, as with any production process, a certain number of rejects will occur which will essentially destroy the entire customization process as customized products would no-longer tally with product bag and respective shipment address. Thus, an automated quality check, such as by automated optical inspection, determines the number of good quality products. If the predetermined number of products has not yet been fulfilled ("NO"), the incomplete order will be placed in the temporary storage system (see 1060) and an order for making replacement product is sent to the production system (1065).

1060—Temporary Storage System

Figure 14:
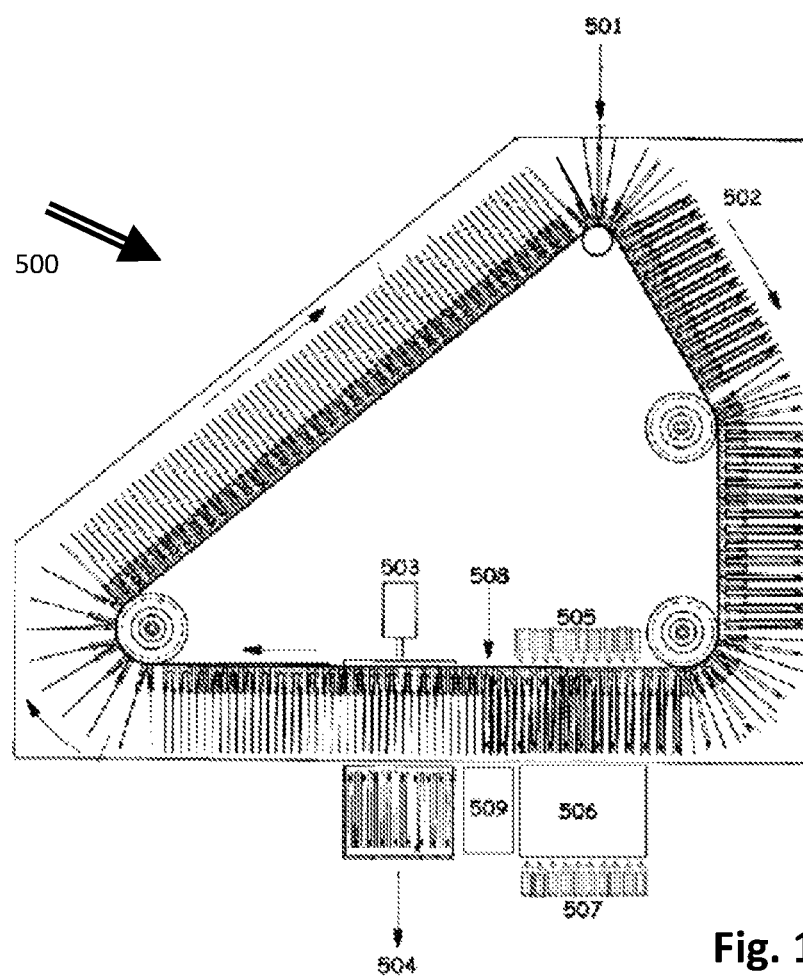
FIG. 14 depicts a stacker set-up suitable for the present invention.

The temporary storage may be achieved by a buffer process as being added in stacking system at a point before final packaging. This is further explained by referring to FIG. 14, schematically depicting exemplarily, but not limiting, a stacker system (500) such as for a diaper manufacturing line. Products may enter a stacker chain at the stacker chain entry area (501), from where the products are transported along a stacker path (502) towards an exit section (504), e.g. a bagging station. At a pushing station, a pushing device (505) has the capability to push any predetermined number of desired products from the stacker chain into a temporary storage system (506), comprising a number of chambers for individual customized products. Once the predetermined number of products is put into the temporary storage another pusher (507) pushes the products back into the stacker chain at a convenient moment in time. which could be for instance when the product in-feed stops, at which point, the packaging systems could continue operation to package the products stored in 506. Optionally further temporary storages can be operated in parallel, here indicated by a further pushing device (508) which pushes further customized products as may be different from the ones in the first temporary storage into a further temporary storage (509), which may be a device similar to the first temporary storage (506). Optionally, either of the first or further temporary storage can be used to store customized products which would later feedback in non-customized products to produce a mixed bag of customized and none customized products.

Optionally one or more secondary buffer systems with a secondary pusher system (508) and a secondary temporary storage (509) may be employed, such as for scenarios where the customizer requires a product shipment consisting of both non-customized and customized products, say a within a pack of 40 diapers, where 5 diapers are selected as travel diapers and as such, have wipes integrated into these 5 diapers which also have a dedicated artwork design, and, 2 diapers in the pack of 40 have a different artwork design for an upcoming babies party, then these 7 diapers, after successful production and quality checks have been performed would be stored in a secondary buffer system (509) and could be re-fed back into a stream of non-customized 33 diapers at a later moment in time to complete the total 40 pack shipment.

1070—Checking for Completeness of Order

Once sufficient products for a customization order have been produced and stored temporarily in the temporary storage system (506), the system can check, if the actual customized product is part of an incomplete earlier order ("YES") or if it is part of a complete order ("NO").

1075—In the first case, the product is added in the temporary storage, optionally awaiting further products until the tally for the order is complete.

1080—In a further waiting step the complete order can now await a suitable slot for being re-introduced into the production process for the standard product.

1085—This re-introduction can suitably be achieved by a further pusher means (507).

1090—Transmitting Product to Packing

For both options, a full set of customized products can now be transferred to the packing station, such as depicted exemplarily in FIG. 14 by a conventional packing pusher system (503) for pushing a predetermined number of products into a pack or a packing system (504) such as a bagging station.

1095—Linking of Address to Product.

To ensure the correct shipment of customized products to the customizer, the final outer packaging system prints dedicated address labels and attaches them to the correctly synced with the customized product SKUs. In some instances the artwork may be printed to the product outer packaging/bag/wrapper/carton/box/container instead of labels being applied, and in some instances the outer packaging/bag/wrapper/carton/box/container may have a transparent window to allow the shipment address to be viewed through the packaging/bag/wrapper/carton/box/container.

1099—Shipment of Customized Products to Shipment Address.

The finish product can then be dispatched and shipped via typical distribution chain directly to the customer.

The invention claimed is:

1. A process for a manufacture of Fast Moving Consumer Good products comprising:
producing a continuous series of a first plurality of products in a continuous main stream production process prior to a packing;
producing a series of between 2 to 10,000 of at least a second plurality of products differing in predetermined customizing features from said first plurality of products in a particular process step within said continuous main stream production process or a side stream production process;
storing and pausing a sub-set or all of said second plurality of products in an interim storage device in a side stream of said continuous main stream production process for between 1 millisecond and 10 years;
re-feeding products of said second plurality of products from said interim storage device back into the continuous main stream production process towards the packing; and
packing a predetermined number of said first plurality of products and a predetermined number of said second plurality of products into a same pack.

2. The process according to claim 1, further comprising:
conveying a portion of said second plurality of products in a machine or cross machine direction to an in-feed of a moving stacker, said moving stacker comprising a plurality of product receiving means adapted to receive at least one product of said portion of said second plurality of products;

sequentially inserting at least one product of said portion of said second plurality of products into at least one of said plurality of product receiving means at the in-feed of the moving stacker such that the portion of said second plurality of products is provided within said plurality of product receiving means;

transporting the portion of said second plurality of products in said plurality of product receiving means towards an extraction station comprising an extraction device;

removing at least one of the portion of said second plurality of products from said plurality of product receiving means of said moving stacker by said extraction device into a temporary storage device; and re-feeding said at least one of the plurality of said second plurality of products stored in said temporary storage device back into the continuous main stream production process or towards a secondary stacker system.

3. The process according to claim 2, wherein the plurality of product receiving means includes at least one of fingers, cassettes, and auger flights.

4. The process according to claim 1, further comprising a "pick & place" process step for customizing at least one of said first plurality of products and said second plurality of products.

5. The process according to claim 4, wherein the "pick & place" process step includes applying an RFID tag to at least one of the first plurality of products and the second plurality of products, a bag having customized products, and a box having customized products.

6. The process according to claim 1, wherein at least one of the first plurality of products and the second plurality of products is a hygienic product, the hygienic product including a top sheet and a back sheet and the process further comprising a step of adding an add-on to the hygienic product, whereby said add-on is located between the top sheet and the back sheet and which has a capability to be removed through either the top sheet or the back sheet or between the top sheet or the back sheet without rendering the hygienic product unusable.

7. The process according to claim 6, wherein the add-on includes at least one of a dry tissue, a wet tissue, and a wipe.

8. The process according to claim 1, wherein the interim storage device includes a plurality of chambers, each of the chambers configured to hold a sub-set or all of said second plurality of products.

9. The process according to claim 1, wherein the interim storage device includes a sealing device configured to selectively fully close and seal the interim storage device to militate against contamination risks.

10. A method for producing customized Fast Moving Consumer Good products concurrently with manufacturing standard products in a main production process stream, the method comprising:
receiving an order from a customizer, said order comprising shipment related data, design related data, and order counts for specific customized products;
converting said design related data into a format compatible with a production process control system;
preparing customized raw materials or product components or product sub-assemblies according to said order in a side stream of said main production process stream;
modifying the main production process stream such that customized products are produced or said customized raw materials or product components or product sub-assemblies are introduced to the main production process stream;
temporarily storing and pausing a sub-set or all of said customized products in an interim storage device in the side stream of said main production process stream for between 1 millisecond and 10 years;
feeding the customized products stored in the interim storage device into the main production process stream, according to one of the order counts for the specific customized products;
packing said customized products into a dedicated customized order pack, according to one of the order counts for the specific customized products or adding said customized products into a pack that comprises non-customized products, according to one of the order counts for the specific customized products;
connecting the customized products with the shipment related data; and
dispatching said customized products to said customizer.

11. The method according to claim 10, further comprising a "pick & place" process step for customizing said customized products.

12. The method according to claim 11, wherein the "pick & place" process step includes applying an RFID tag to at least one of said customized products, a bag having customized products, and a box having customized products.

13. The method according to claim 10, wherein at least one of the customized products is a hygienic product, the hygienic product including a top sheet and a back sheet, and wherein the method further comprising a step of adding an add-on to the hygienic product, whereby said add-on is located between the top sheet and the back sheet and which has a capability to be removed through either the top sheet or the back sheet or between the top sheet or the back sheet without rendering the hygienic product unusable.

14. The method according to claim 13, wherein the addon includes at least one of a dry tissue, a wet tissue, and a wipe.

* * * * *